(12) United States Patent
Pregenzer et al.

(10) Patent No.: US 8,753,253 B2
(45) Date of Patent: Jun. 17, 2014

(54) SEPARATOR FOR SEPARATING AIR AND SOLIDS FROM A DENTAL WASTE WATER MIXTURE

(76) Inventors: Bruno Pregenzer, Mieming (AT); Alfred Konzett, Patsch (AT)

( * ) Notice: Subject to any disclaimer, the term of this patent is extended or adjusted under 35 U.S.C. 154(b) by 1087 days.

(21) Appl. No.: 12/670,813

(22) PCT Filed: Jul. 28, 2008

(86) PCT No.: PCT/EP2008/006208
§ 371 (c)(1),
(2), (4) Date: Jan. 26, 2010

(87) PCT Pub. No.: WO2009/015853
PCT Pub. Date: Feb. 5, 2009

(65) Prior Publication Data
US 2010/0204032 A1  Aug. 12, 2010

(30) Foreign Application Priority Data
Jul. 27, 2007  (AT) ................................ A 1189/2007

(51) Int. Cl.
*B04B 11/06* (2006.01)
*B04B 15/02* (2006.01)
*B04B 15/08* (2006.01)
*A61C 17/06* (2006.01)
*B04B 9/04* (2006.01)

(52) U.S. Cl.
USPC ................. 494/14; 494/42; 494/64; 494/67; 494/84

(58) Field of Classification Search
USPC ........... 494/14, 26, 31–35, 42–43, 83–84, 50, 494/51, 63, 64, 67, 80; 433/92; 74/462, 466
See application file for complete search history.

(56) References Cited

U.S. PATENT DOCUMENTS

| | | | | |
|---|---|---|---|---|
| 1,954,676 A | * | 4/1934 | Lindberg | 494/56 |
| 2,182,159 A | * | 12/1939 | Miller et al. | 494/14 |
| 3,570,754 A | * | 3/1971 | Kirkpatrick | 494/7 |
| 4,193,536 A | | 3/1980 | Kubota | |
| 4,356,959 A | * | 11/1982 | Rosander | 494/60 |
| 4,663,035 A | * | 5/1987 | Rosander | 210/167.01 |
| 4,753,632 A | * | 6/1988 | Hofmann et al. | 494/43 |
| 4,842,478 A | * | 6/1989 | Durr et al. | 415/169.2 |
| 4,891,041 A | * | 1/1990 | Hohmann et al. | 494/62 |

(Continued)

FOREIGN PATENT DOCUMENTS

| | | |
|---|---|---|
| AT | 389471 | 5/1989 |
| CH | 238684 | 8/1945 |

(Continued)

*Primary Examiner* — Charles E Cooley
(74) *Attorney, Agent, or Firm* — Dilworth & Barrese, LLP.

(57) ABSTRACT

The present invention relates to a separator for separating air and possibly present solids from a mixture of dental waste water, comprising an air-water separator, wherein a mixture supply tube opens into a centrifuge drum, an air discharge duct extends from the centrifuge drum to the mixture supply tube and the centrifuge drum includes an upper drain edge over which a water outlet is guided onto the outside of the centrifuge drum. In accordance with the invention, the separator is characterized in that the mixture supply tube opens onto a central turbine wheel arranged above the centrifuge drum bottom and an impeller of a waste water delivery pump, which communicates with the water outlet, is arranged on an outside of the centrifuge drum in the vicinity of the centrifuge drum bottom.

43 Claims, 9 Drawing Sheets

(56) References Cited

U.S. PATENT DOCUMENTS

| | | | |
|---|---|---|---|
| 4,932,933 A * | 6/1990 | Becker et al. | 494/62 |
| 5,330,641 A * | 7/1994 | Cattani | 210/188 |
| 5,421,996 A * | 6/1995 | Trawoger et al. | 210/86 |
| 5,484,282 A * | 1/1996 | Trawoger et al. | 433/92 |
| 5,613,851 A * | 3/1997 | Trawoger et al. | 433/92 |
| 6,372,006 B1 * | 4/2002 | Pregenzer et al. | 55/406 |
| 8,342,822 B2 * | 1/2013 | Thoms et al. | 417/423.7 |
| 2009/0298011 A1 * | 12/2009 | Thoms et al. | 433/92 |
| 2010/0034673 A1 * | 2/2010 | Thoms et al. | 417/313 |
| 2010/0204032 A1 * | 8/2010 | Pregenzer et al. | 494/14 |

FOREIGN PATENT DOCUMENTS

| | | | |
|---|---|---|---|
| EP | 290745 | 11/1988 | |
| EP | 524455 A1 * | 1/1993 | A61C 17/06 |
| EP | 642771 A2 * | 3/1995 | A61C 17/06 |
| EP | 1285636 A2 * | 2/2003 | |
| GB | 252173 | 10/1926 | |
| WO | WO 8904152 A1 * | 5/1989 | A61C 17/04 |

\* cited by examiner

SEPARATOR FOR SEPARATING AIR AND SOLIDS FROM A DENTAL WASTE WATER MIXTURE

BACKGROUND OF THE INVENTION

The present invention relates to a separator for separating air and possibly present solids from a mixture of dental waste water, comprising an air-water separator, wherein a mixture supply tube opens into a centrifuge drum, an air discharge duct extends from a centrifuge drum to the mixture supply tube, and the centrifuge drum has an upper draining edge over which a water outlet is guided onto the outside of the centrifuge drum. There can be provided a solids separator, which is arranged one inside the other with the air-water separator and can include at least one solids blocking flange on the centrifuge drum shell surface.

Such separators, by means of which the waste water mixtures obtained at dental work stations, which beside water and air frequently also contain solids such as amalgam, ceramics, etc., can be split up into their constituents and be disposed of separately, are known in a variety of configurations. Such separators frequently are integrated in the base cabinet of a spittoon cup of the dental work station or in some other built-in furniture, so that a compact construction is required, wherein in particular the axial length of the separators is important, in order to be able to work also with little slope available or with a limited installation height. Therefore, it recently has been proposed to arrange the air/water separator and the solids separator lying coaxially one inside the other, i.e. to nest the same radially inside each other so to speak, whereby the necessary construction size can be reduced considerably. DE 39 16 742 and DE 39 43 819 for example show such arrangements nested inside each other.

Here, it is advantageous to introduce a mixture supply tube into the centrifuge drum from above and subject the emerging waste water mixture in the centrifuge drum to a sufficient radial acceleration, so that the liquid and solid constituents of the waste water mixture run onto the centrifuge drum shell surface, whereas the air from the waste water mixture can be discharged from the centrifuge drum in upward direction opposite to the mixture supply tube. While the solids are retained by a corresponding solids blocking flange at the inner shell surface of the centrifuge drum, the water or the liquid from the waste water mixture can escape over this solids blocking flange via the upper surface of the centrifuge drum. There, it usually is removed with a water delivery pump, wherein it is known to arrange an impeller with a blade rim at the upper edge of the centrifuge drum.

However, such separators with nested construction frequently are difficult to clean or difficult to demount and mount again. In addition, considerable loads of the centrifuge drum are obtained in part, which involve a tendency to tumbling, which must be overcome with in part expensive bearing measures.

SUMMARY OF THE INVENTION

Proceeding herefrom, it is the object underlying the present invention to create an improved separator as mentioned above, which avoids the disadvantages of the prior art and develops the latter in an advantageous way. Preferably, an arrangement easy to clean and with little tendency to tumbling should be created, without impairing an efficient separation of the mixture constituents.

In accordance with the invention, this object is solved by a separator according to the description herein. Preferred aspects of the invention are also subject-matter herein In accordance with the invention, it hence is proposed to centrally concentrate the load-intensive components exposed more to forces from the waste water, and possibly also the more weight-intensive components, at the bottom of the centrifuge drum, in order to achieve a favorable weight distribution of the entire arrangement of the moving components. In accordance with the invention, the mixture supply tube opens onto a central turbine wheel arranged above the centrifuge drum bottom, wherein a water delivery pump is arranged on an outside of the centrifuge drum in the vicinity of the centrifuge drum bottom. This results in a low center of gravity and a favorable weight distribution, which leads to a low tendency to tumbling of the rotating parts and hence allows a light-weight bearing. Nevertheless, an extremely efficient separation of the air and liquid or solid constituents of the waste water mixture can be achieved by the central turbine wheel, onto which the mixture supply tube opens directly. The turbine wheel flings away the liquid and solid constituents with a high speed, whereas the air or the gaseous constituents of the waste water mixture can be discharged from the centrifuge drum opposite to the mixture supply tube.

In accordance with an advantageous development of the invention, the turbine wheel, the centrifuge drum and the impeller of the waste water delivery pump form a mounting unit, which advantageously can be removed as a whole from the separator housing part accommodating the mixture supply tube. In this way, an easy cleaning and maintenance of the separator can be achieved, since the entire rotating unit can be removed as such. In particular, separate solid outlet openings in the centrifuge drum can be omitted due to this convenient removability, since for removing the accumulated solids it is merely necessary to take out said mounting unit, so that the solids can be removed from the centrifuge drum.

Advantageously, said mounting unit comprises a cup-shaped assembly carrier, which forms a separator housing part which on the one hand is releasably attached to the aforementioned separator housing part and on the other hand rotatably carries or accommodates the impeller of the waste water delivery pump, the centrifuge drum and the turbine wheel. For removing the rotating components turbine wheel and centrifuge drum, which are combined to one assembly, it is merely necessary to detach the assembly carrier from the remaining separator housing, so that the entire mounting unit can be removed.

In accordance with a development of the invention, the impeller of the waste water delivery pump on the one hand and the centrifuge drum and the turbine wheel connected therewith on the other hand are releasably connected with each other. The impeller of the waste water delivery pump can be attached to a hub and/or shaft piece and/or be formed in one piece with this integral unit. The same is rotatably mounted on the aforementioned separator housing part, which forms the assembly carrier of the mounting unit.

In principle, the centrifuge drum likewise can be mounted on said hub and/or shaft piece. Advantageously, however, the bottom of the centrifuge drum can non-rotatably be connected to the aforementioned impeller of the waste water delivery pump. Advantageously, releasable quick-acting closure means are provided, which can be actuated tool-free and by means of which the centrifuge drum can quickly and easily be attached to the impeller of the waste water delivery pump and can easily be detached from the same, for example for the purpose of cleaning the centrifuge drum. In principle, said quick-acting closure means can have different configurations.

According to an advantageous embodiment, the quick-acting closure means can constitute a spring-biased bayonet lock which at the bottom of the centrifuge drum and on an axial end face of the impeller includes locking protrusions and locking recesses cooperating therewith, which can be inserted in each other by an axial plug-in movement and can be locked with each other by a relative rotation of centrifuge drum and impeller. Advantageously, a biasing means for example in the form of a coil spring is provided between impeller and centrifuge drum, in order to ensure a backlash-free rigid connection of the two components with each other.

In a furthermore advantageous embodiment of the invention, the turbine wheel seated in the interior of the centrifuge drum in turn is directly, preferably releasably attached to the bottom of the centrifuge drum. For example, the turbine wheel can be screwed to the bottom of the centrifuge drum. Due to the turbine wheel seated directly on the bottom of the centrifuge drum a concentration of the center of gravity of the rotating components is achieved in the best possible way.

To achieve a light-weight and yet stable bearing of the rotating components of the separator in accordance with an advantageous embodiment of the invention, the impeller of the waste water delivery pump, the centrifuge drum attached thereto and the turbine wheel again attached to the same can rotatably be attached to a central hub piece, which includes a coupling piece for coupling to a common rotary drive. Said hub piece advantageously is rotatably accommodated in the assembly carrier forming a housing part, wherein the rotary drive can releasably be attached to the assembly carrier by means of a housing piece and can releasably be coupled with a drive shaft by means of said hub piece. Preferably, the assembly carrier constituting a lid comprises a central connecting flange on its end face, to which the rotary drive can preferably rigidly be connected by means of an end-face housing portion.

In accordance with a development of the invention it can be provided that the hub piece includes fastening means for the rigid attachment of the drive shaft of the rotary drive. The hub piece can be mounted on the assembly carrier constituting a lid by means of a pivot bearing preferably in the form of at least one pivot bearing. Alternatively or in addition, the bearings of the rotary drive, i.e. of the drive shaft with respect to the body of the rotary drive, can be utilized to mount the rotating separator components with respect to the separator housing or the assembly carrier constituting a lid. If on the one hand the aforementioned hub piece is rigidly connected with the drive shaft and on the other hand the rotary drive housing is rigidly connected with the assembly carrier constituting a lid, the bearings of the drive shaft of the rotary drive at the same time can effect the bearing of the hub piece and of the rotatable separator components attached thereto.

Hence, the centrifuge drum along with the turbine wheel connected therewith and the impeller advantageously is mounted on a central bottom portion by only one central pivot bearing below the drum bottom.

To achieve an efficient waste water delivery and on the other hand a compact construction, it is advantageous when the impeller of the waste water delivery pump includes a blade rim, which is arranged at the outer edge of the centrifuge drum bottom. Advantageously, the impeller of the waste water delivery pump includes an axial inlet region, with which the impeller is seated below the centrifuge drum bottom at its outer edge portion, so that an annular portion of the water outlet surrounding the centrifuge drum shell surface can open directly onto the axial inlet region of the impeller.

To achieve a particularly compact construction, the impeller advantageously has a radial drainage region. In this way, a waste water outlet port substantially can be provided directly below the centrifuge drum bottom at the level of the impeller arranged there, whereby a generally small slope, for instance below a spittoon cup of a dental work station, is sufficient.

In accordance with a development of the invention, the turbine wheel arranged in the centrifuge drum also has an axial inlet region and a radial outlet region, so that the waste water mixtures introduced axially, i.e. substantially parallel to the axis of rotation of the centrifuge drum and of the turbine wheel, undergo a deflection in the turbine wheel and are flung towards the shell surface of the centrifuge drum substantially transverse to said axis of rotation.

To achieve an efficient introduction of the waste water mixture into the turbine wheel, it is provided in accordance with a development of the invention that the mixture supply tube is guided directly up to the inlet region of the turbine wheel, wherein the turbine wheel and the mixture supply tube can engage in each other for example by means of annular pockets.

In accordance with a development of the invention, the mixture supply tube is arranged vertically, so that the turbine wheel rotates relative to the mixture supply tube. Correspondingly, the mixture supply tube need not have any expensive sealing means at its housing outlet, as is the case with co-rotating mixture supply tubes.

To achieve a generally particularly compact arrangement, the mixture supply tube preferably is coaxially accommodated in the air discharge duct, which is guided out of the centrifuge drum opposite to the mixture supply tube. It should be appreciated that the air discharge duct need not be guided out of the centrifuge drum coaxially to the mixture supply tube and/or coaxially to the axis of rotation of the centrifuge drum along its entire length. In accordance with a preferred development of the invention, the air discharge duct comprises an air outlet guided out of the separator housing radially or transverse to the axis of rotation of the centrifuge drum above the centrifuge drum.

To achieve an axially particularly compact configuration, a separate fan wheel for cooling the motor driving the centrifuge drum advantageously can be omitted, so that with its winding portion or the housing surrounding the same said motor can directly be seated below the aforementioned assembly carrier, which acts as a lid for the impeller of the waste water delivery pump. By omitting a cooling fan wheel between motor and centrifuge drum, the axial construction can be shortened. To nevertheless achieve a sufficient cooling of the motor, it is provided in accordance with a further aspect of the present invention that the air discharge duct guided out of the centrifuge drum constitutes a cooling air duct for cooling said motor. In particular, said air discharge duct can at least partly be guided over the motor, around the motor and/or advantageously through the motor, so that the air discharged from the centrifuge drum is cooling the motor. The air guided through the air discharge duct need not necessarily be guided completely onto the motor or its heat-producing regions. For example, the air discharge duct can include a branch, so that part of the air discharged is used for cooling and the remaining part is discharged directly. To achieve a maximum cooling efficiency in accordance with a preferred embodiment of the invention, the entire air discharge duct is, however, guided through a housing portion surrounding the winding of the motor, in order to dissipate the heat produced in the motor winding in the best possible way.

Advantageously, the air discharge duct can include two approximately half-shell-shaped cooling air duct portions which closely envelop the winding of the motor or a housing portion including the winding, wherein in accordance with an advantageous embodiment of the invention said half-shell-shaped cooling air duct portions can be traversed in opposite directions. In accordance with a development of the invention, the blower effecting the discharge of air, which advantageously likewise is driven by the motor driving the centrifuge drum, can be arranged on the side of the motor opposite the centrifuge drum, wherein in accordance with an advantageous embodiment of the invention the air discharge duct coming from the centrifuge drum is guided into the motor housing at an end portion of the motor housing facing the centrifuge drum, is guided along the winding portion of the motor and is connected with the blower. To achieve an axially short configuration, it advantageously is provided that the air discharge duct coming from the centrifuge drum is guided radially into the motor housing, or the waste air duct of the blower is radially guided out of the motor housing.

Advantageously, the air discharge or cooling air duct guided around the motor or its winding performs a dual function in that it not only cools the motor, but also minimizes its noise emission. In accordance with a development of the invention, said air discharge duct can at least partly constitute a muffler and/or be provided with sound-absorbing means, in particular in the portion surrounding the motor. In a particularly advantageous way, it can be provided that the aforementioned half-shell-shaped cooling air duct portions surrounding the motor winding are boarded with a sound- and/or heat-insulating material.

To make the separation of solids in the centrifuge drum particularly efficient, a plurality of solids blocking flanges arranged one above the other can be arranged in the centrifuge drum. If a solid succeeds in getting over a first solids blocking flange, the next solids blocking flange or the solids blocking flange after that etc. will capture the same.

In accordance with a development of the invention, the solids blocking flanges arranged one above the other are formed differently, wherein various deviations in shape are possible in principle. It would of course also be possible in principle to provide the plurality of solids blocking flanges with the same shape. A more efficient separation of solids can, however, be achieved by differently formed solids blocking flanges.

In accordance with a development of the invention, a solids blocking flange located closer to the centrifuge drum bottom has an overflow edge located radially further to the inside than a further solids blocking flange arranged above this solids blocking flange. The solids blocking flange located closer to the centrifuge drum bottom can form an inclined surface sloping radially to the inside, towards the centrifuge drum bottom, whereas a solids blocking flange located at the upper edge of the centrifuge drum is bent as seen in cross-section and includes an inner web or inner flange hanging downwards towards the centrifuge drum bottom.

To avoid losses in the degree of separation as a result of entrainment effects during the start of the separator, a water remover is provided in accordance with a development of the invention, which during standstill of the centrifuge drum removes the liquid accumulated therein. Advantageously, the water remover can act as temporary reservoir and during or after restart of the centrifuge drum can feed the liquid removed from the centrifuge drum back into the same. Due to the temporary removal of the liquid stored in the centrifuge drum during standstill of the centrifuge drum, the liquid is prevented from spilling over the edge of the centrifuge drum during restart. In addition, vibration and tumbling loads of the centrifuge drum during the start are reduced. In principle, the water remover can have different constructions. In accordance with an advantageous embodiment of the invention, the water remover can include a volume-variable temporary reservoir, preferably in the form of a bellows reservoir, which can be varied in terms of its volume by a suitable actuator, in order to suck liquid out of the centrifuge drum or return it to the same.

Advantageously, the removal of water is effected automatically by a suitable control means, for example in dependence on the rotational speed of the centrifuge drum, so that the water can be removed during its standstill and can be returned to the same during its start.

In accordance with a development of the invention, the filling level of the centrifuge can also be monitored, for example by a sensor detecting the liquid level in the centrifuge drum and/or by a sensor detecting the solid filling, for example in the form of a light sensor detecting the radial deposition of solids.

BRIEF DESCRIPTION OF THE DRAWINGS

The invention will be explained in detail below with reference to a preferred embodiment and associated drawings, in which.

DESCRIPTION OF THE PREFERRED EMBODIMENTS

Figure 1:
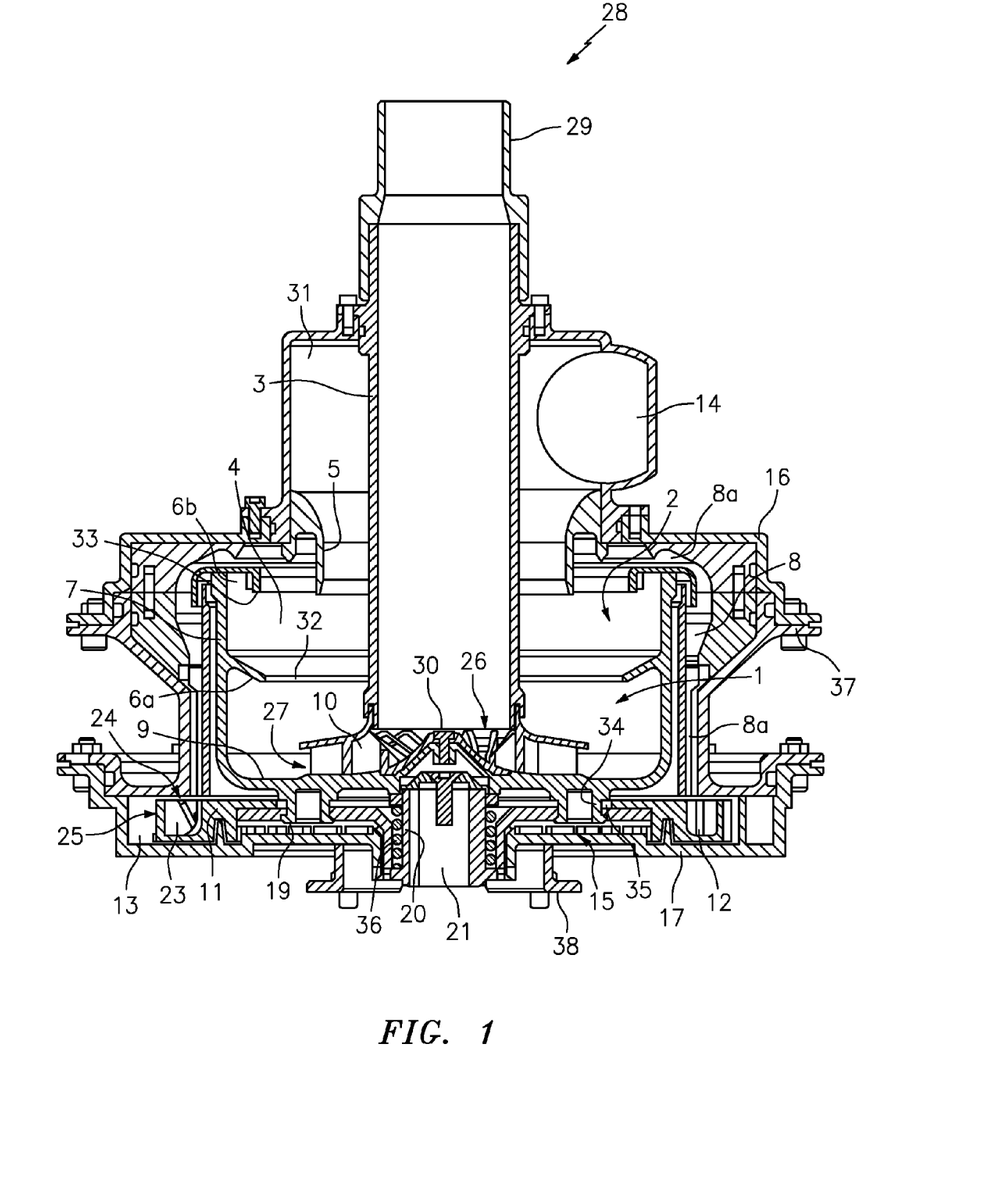
FIG. 1: shows a longitudinal section through a separator in accordance with a preferred embodiment of the invention.

The separator shown in FIG. 1 comprises a multi-part separator housing 16 divided into various axial portions, which on its upper end face 28 includes a waste water mixture port 29, through which the waste water mixture to be decomposed into its constituents can be introduced. As shown in FIG. 1, said waste water mixture port 29 leads into a central mixture supply tube 3 coaxial to the axis of rotation of the centrifuge drum 4 yet to be described in detail, which leads into the interior of the centrifuge drum 4 substantially vertically and opens there above the bottom 9 of the centrifuge drum 4. With its lower orifice region, said mixture supply tube 3 is seated on the inlet region 24 of a turbine wheel 10 which is directly attached to the substantially flat bottom 9 of the centrifuge drum 4. As shown in FIG. 1, the bottom 9 of the centrifuge drum 4 also partly forms a wall of the turbine wheel 10, which is firmly, but releasably attached to the centrifuge drum bottom 9 by a central fastening means 30 in the form of a threaded bolt. The turbine wheel 10 is of the axial/radial type, so that the waste water mixtures introduced via the axial inlet region 26 are flung out of the turbine wheel 10 via the radial outlet 27.

As shown in FIG. 1, the mixture supply tube 3 and the inlet region 24 of the turbine wheel 10 are annularly seated one inside the other. In the illustrated embodiment, the mixture supply tube 3 has an annular plug-in pocket in which an annular land of the turbine wheel 10 engages, which protrudes on its end face. The turbine wheel 10 is rotatable with respect to the mixture supply tube 3, which is stationarily attached to the separator housing 16.

As shown in FIG. 1, the radial outlet region 27 of the turbine wheel 10 is arranged directly above the bottom 9 of the centrifuge drum 4, so that liquid and solid constituents of the waste water mixture emerging from the turbine wheel 10 are passed over the bottom 9 to the shell surface 7 of the centrifuge drum. While the solids and the liquid constituents rise upwards along the inner wall of the substantially cylindrical, in particular circularly cylindrical shell surface 7, the air of the waste water mixture separated from the liquid and solid constituents inside the centrifuge drum 4, which due to the spin generated by the turbine wheel 10 and the corresponding kinetic energy as well as the centrifugal acceleration caused by the centrifuge drum 4 can efficiently be separated from the liquid and solid constituents, can be guided upwards out of the centrifuge drum 4 opposite to the mixture supply tube 3. As shown in FIG. 1, an air discharge duct 5 extends coaxially around the mixture supply tube 3 and opens into a housing space 31, from which an air outlet 14 is guided out of the separator housing 16 radially or tangentially.

As shown in FIG. 1, two solids blocking flanges 6a and 6b protrude radially inwards from the inside of the centrifuge drum shell surface 7, wherein the first solids blocking flange 6a located further down forms a conical surface sloping towards the centrifuge drum bottom 9 and has an overflow edge 32 located radially further to the inside than the second solids blocking flange 6b arranged at the upper end of the centrifuge drum 4. The latter has an inner edge 33 hanging downwards, which with the roof portion of the solids blocking flange 6b forms a second storage space for solids which have succeeded in getting over the first solids blocking flange 6a.

While the solids are collected at the two solids blocking flanges 6a and 6b, the water or the liquid constituent of the waste water mixture can rise over the upper edge of the centrifuge drum 4 and get over the same into the water outlet 8, which initially consists of a disk-shaped space between said upper solids blocking flange 6b and a corresponding housing portion and then merges into a ring-shaped outlet duct 8a, which extends between the outer shell surface of the centrifuge drum 4 and the housing portion surrounding the latter, cf. FIG. 1.

At the lower end of the centrifuge shell surface 7 said annular portion of the water outlet 8a opens onto a blade rim 23 of an impeller 11 of a waste water delivery pump 12 which extends on the outside of the centrifuge drum 4 directly below its bottom 9. The blade rim 23 is located approximately in the transition region between the centrifuge drum bottom and the centrifuge drum shell surface 7, cf. FIG. 1. The impeller 11 likewise is of the axial/radial type. The waste water entering via the axial inlet region 24 is discharged via the radial outlet region 25 and can exit from the separator housing 16 via a waste water outlet 13 approximately at the level of the impeller 11.

As shown in FIG. 1, the impeller 11 also is directly connected with the bottom 9 of the centrifuge drum 4, namely via quick-acting closure means 19 to be actuated tool-free in the form of a spring-biased bayonet lock which includes locking protrusions 34 protruding from the centrifuge drum bottom 9, which are distributed around the periphery of the centrifuge drum 4 at a distance from its axis of rotation. Inside the impeller 11, there are provided locking recesses 35 cooperating therewith, which form a keyhole so to speak for the locking protrusions 34 and can be brought in engagement by the impeller 11 sitting axially on the centrifuge drum bottom 9. By slightly rotating the same, they can then be caused to lock.

As shown in FIG. 1, a central hub piece 20 is locked at the impeller 11, which includes a coupling piece 21 in the form of a central shaft recess. Between the hub piece 20 and the centrifuge drum bottom 9, a spring 36 is provided for bracing the components held together by the quick-acting closure means 19.

The centrifuge drum 4, the turbine wheel 10 attached thereto and the impeller carrying the centrifuge drum 4 together with the hub piece 20 form a mounting unit 15 which is seated on an assembly carrier forming a housing part 17, which generally is formed approximately like a cup and comprises a lateral mounting flange 37, by means of which the housing part 17 can releasably be attached to the rest of the separator housing 16, cf. FIG. 1. The housing part 17 carries the above-described mounting assembly 15 or forms a part thereof, which can be removed as a whole upon detaching the mounting flange 37 from the remaining separator housing 16, which surrounds the mixture supply tube 3.

Figure 2:
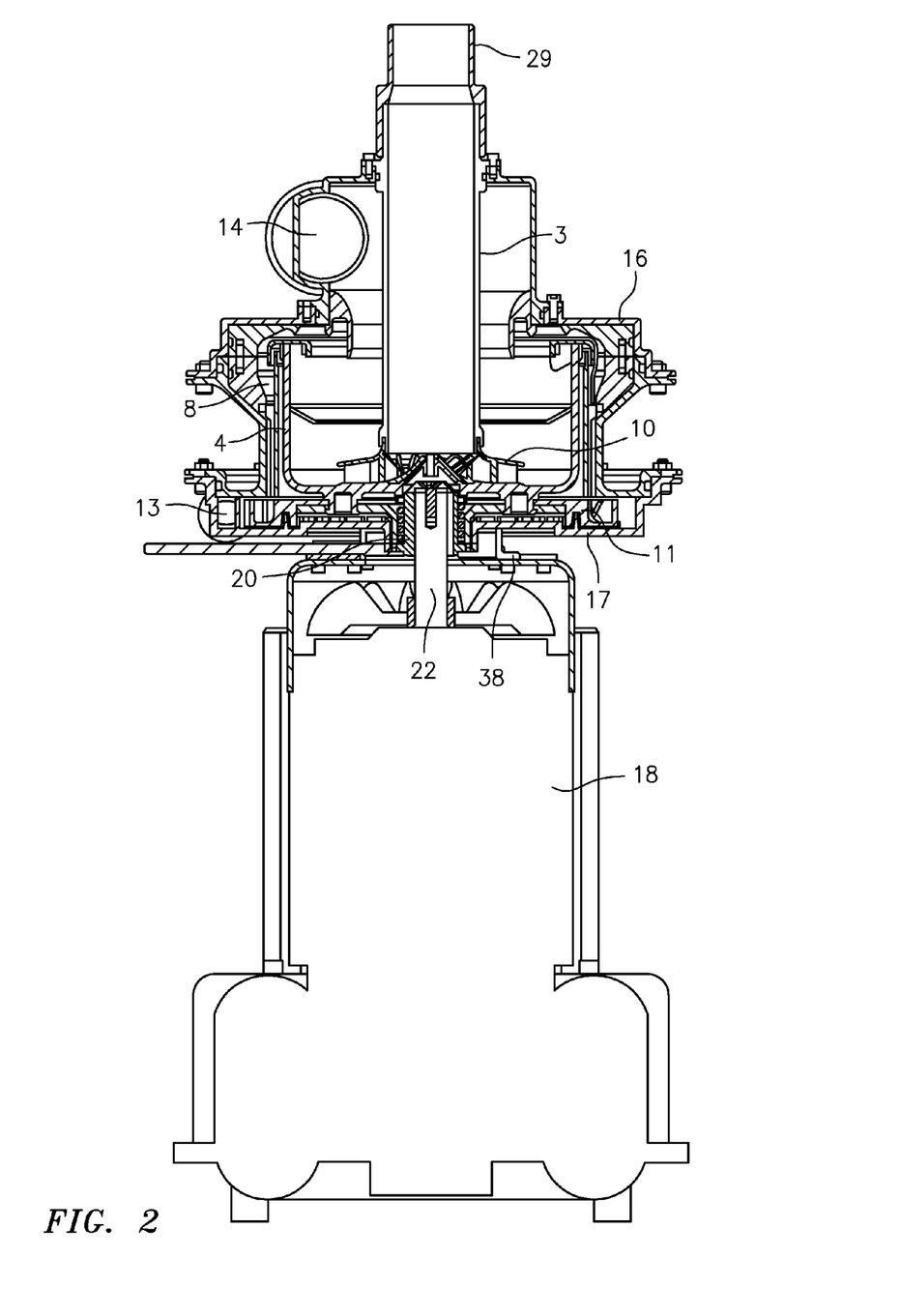
FIG. 2: shows the separator from FIG. 1 with a rotary drive mounted thereto.

As shown in FIG. 1, the housing part 17 comprises a connecting piece 38 around the hub piece 20, to which the rotary drive 18 shown in FIG. 2 or its end-face housing portion can rigidly be attached. The rotary drive 18 advantageously comprises a protruding drive shaft.

Figure 4:
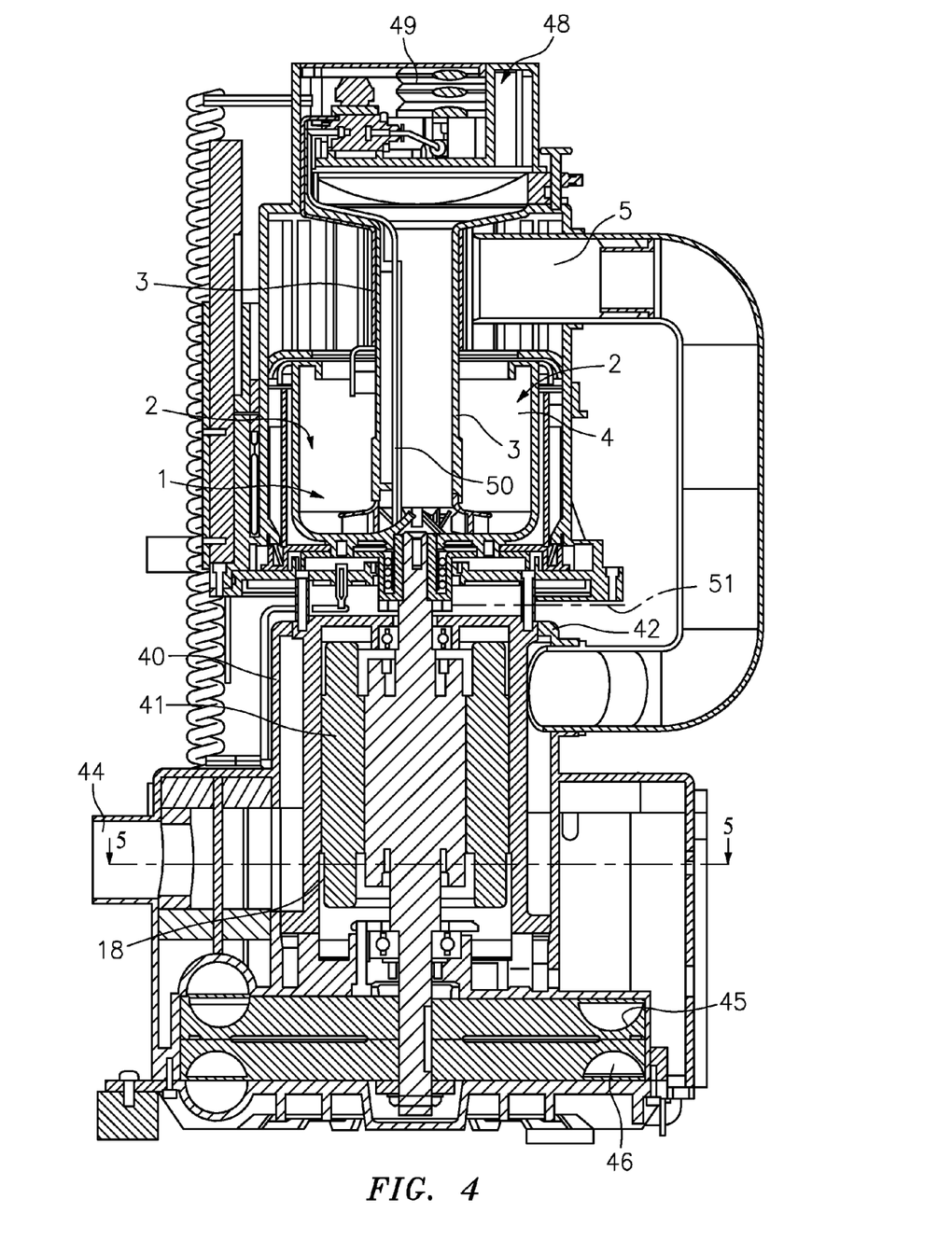
Figure 5:
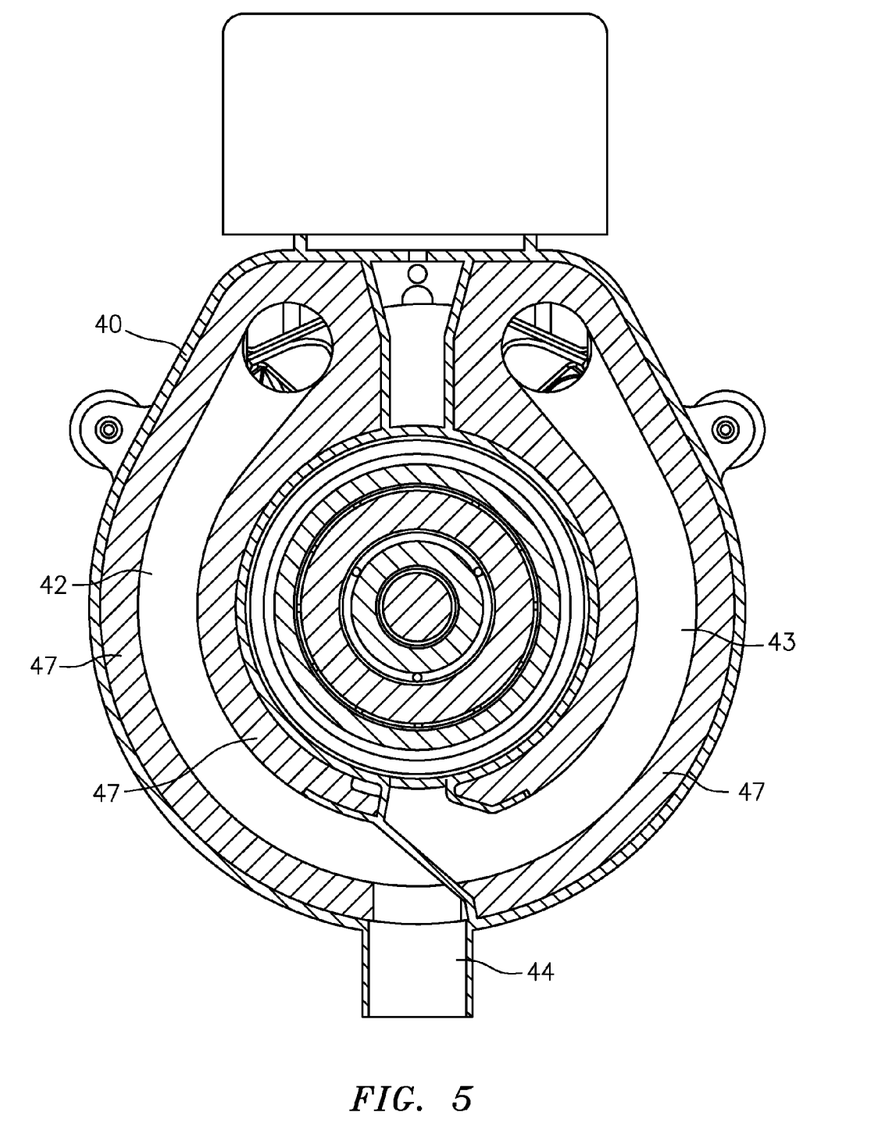
FIG. 5: shows a cross-section through the motor and the cooling air duct surrounding the same along line 5-5 in FIG. 4, FIG. 6: shows a non-sectional side view of the separator from the preceding Figures.
Figure 6:
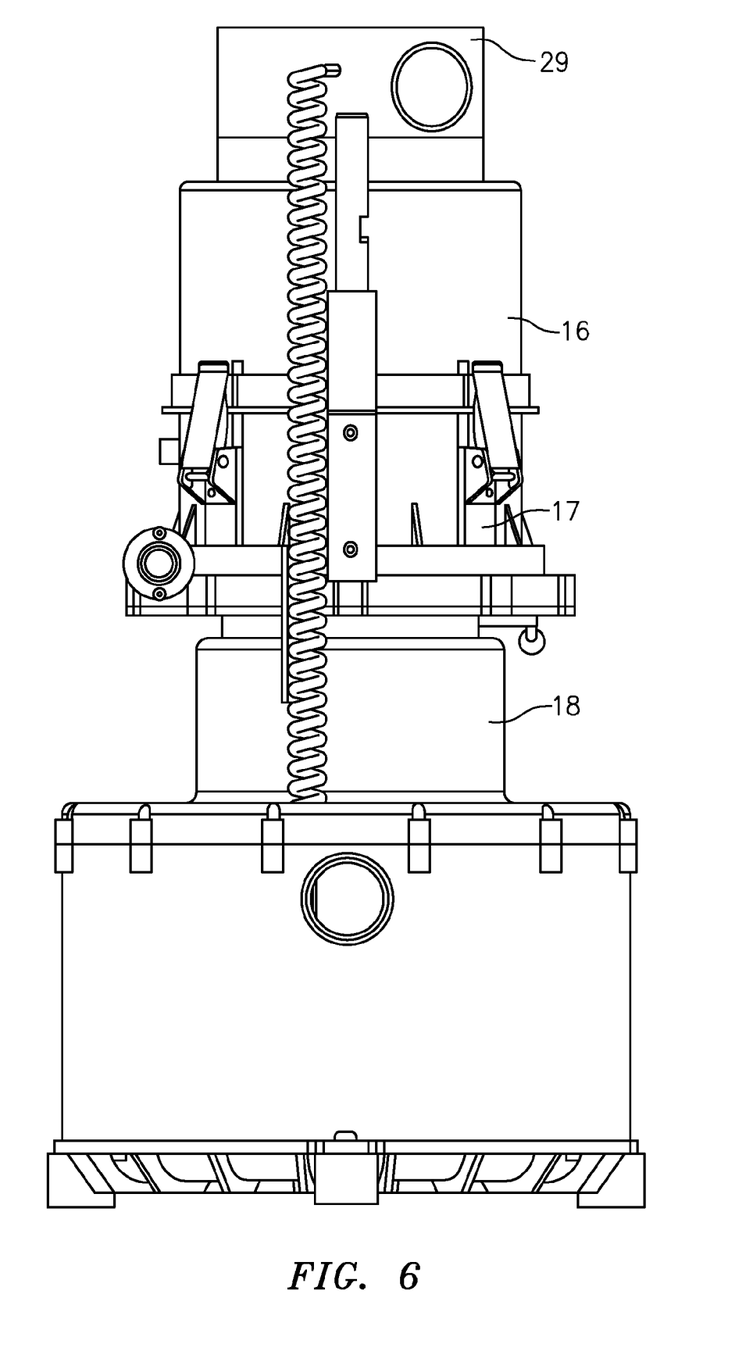

FIGS. 4 to 6 show a further advantageous embodiment of a separator, which in many parts corresponds to the embodiment described above, so that for corresponding components corresponding reference numerals are used and in so far reference is made to the preceding description.

Figure 3:
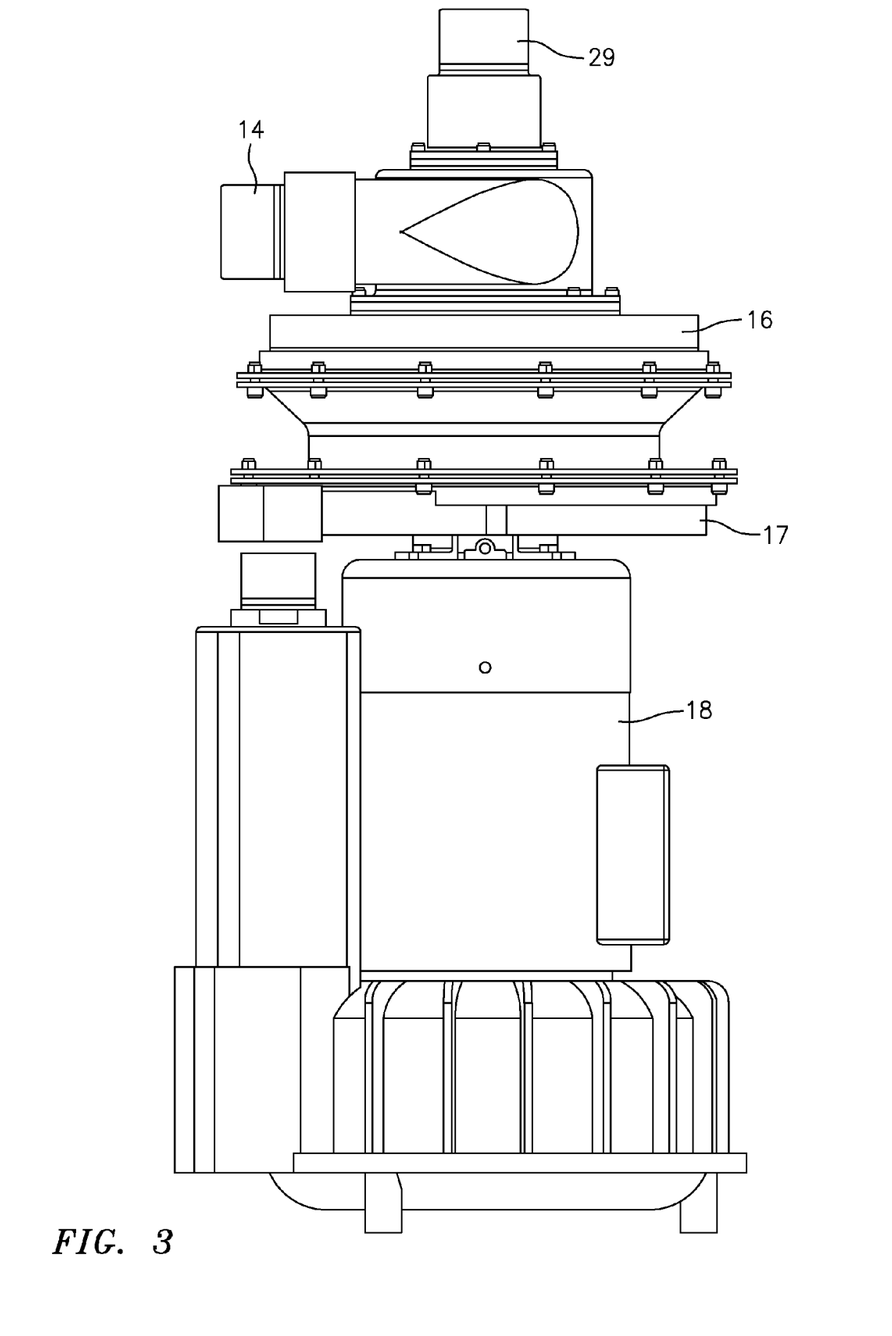
FIG. 3: shows a non-sectional side view of the separator and of the attached rotary drive from FIG. 2, FIG. 4: shows a longitudinal section through a separator in accordance with another preferred embodiment of the invention, in which the air discharge duct is guided out of the centrifuge drum through the housing of the motor for cooling the same.

An essential difference of the embodiment as shown in FIGS. 4 to 6 as compared to the embodiment as shown in FIGS. 1 to 3 is the discharge of the air separated in the air-water separator 1. As is shown in particular in FIG. 4, the air discharge duct 5 partly constitutes a cooling air duct, in order to cool the motor 18 driving the centrifuge drum 4. In particular, the air discharge duct 5 is introduced into the motor housing 40 at an upper end of the motor housing 40, which directly adjoins the lid 17, wherein the air discharge duct 5 advantageously is guided radially into said motor housing 40, cf. FIG. 4, whereby an axially compact construction can be achieved. Furthermore, in contrast to the embodiment of FIG. 2, a separate fan wheel for cooling the motor 18 is omitted, i.e. cooling the motor 18 is effected alone via the stream of air sucked off from the centrifuge drum 4.

As is shown best in FIG. 5, the motor portion including the winding 41 of the motor 18 is surrounded by two half-shell-shaped cooling air duct portions 42, 43, one of which is connected with the air discharge duct 5 and the other one is connected with the waste air duct 44. Both cooling air duct portions 42 and 43 are connected with a compressor wheel or impeller 45 of the waste air blower, which sucks off the air separated in the centrifuge drum 4 via the air discharge duct 5 and discharges the same via said waste air duct 44. The waste air blower 46 likewise is driven by the motor 18 which drives the centrifuge drum 4, wherein the waste air blower 46 is arranged on the side of the motor 18 opposite the centrifuge drum 4. The aforementioned compressor wheel or impeller 45 is seated on the motor axle, on which there is also seated the centrifuge drum 4 or the coupling piece 21 connected therewith.

Advantageously, the air discharge duct 5 is provided with a sound and/or heat insulation in the vicinity of the motor, in particular in the vicinity of the aforementioned cooling air duct portions 42 and 43. As shown in FIG. 5, the two cooling air duct portions 42 and 43, which surround the motor 18 or its winding, each are lined on the wall side with insulating material 47, so that a sound insulation can be achieved at the same time via the cooling air duct.

To ensure a trouble-free start of the separator, the liquid separated in the centrifuge drum 4 can be removed from the same during a standstill of the centrifuge drum, so that a spillover or swing-up of the centrifuge drum 4 is prevented during the start. In the illustrated embodiment of FIG. 4, a water remover 48 is provided for this purpose, which in the illustrated embodiment is arranged on the upper surface of the separator. The water remover 48 advantageously can comprise a temporary reservoir 49, which advantageously is variable in volume, in particular can be designed in the form of corrugated bellows, so that by varying the volume of the temporary reservoir the liquid stored in the centrifuge drum 4 can be sucked off. It should be appreciated, however, that other configurations of the water remover also are possible in principle, for example a separate pump which delivers into a reservoir.

The water remover 48 advantageously comprises a suction line 50 shown in FIG. 4, which with one end extends to the bottom of the centrifuge drum 4, in particular in the vicinity of the turbine wheel 10, and with its other end is connected with the aforementioned corrugated bellows.

Advantageously, the water remover 48 is actuated by a control device not shown especially in the Figures, which automatically starts the water remover 48 when the separator is shut off or the centrifuge drum 4 stops, in order to suck off liquid separated in the centrifuge drum 4. During or after restart of the centrifuge, the water or the liquid, respectively, is returned to the centrifuge drum 4.

Furthermore, a pin-shaped latch 51 is schematically shown in FIG. 4, by means of which the motor 18 can be blocked in a predetermined position. For this purpose, the pin-shaped latch 51 is moved radially to the inside, in order to snap into a corresponding recess. In this way, the centrifuge drum 4 can be turned off in a simple way.

As shown in FIG. 6, the upper housing part 16 and the lower housing part 17 can be connected with each other by means of quick-acting clamping means, preferably in the form of clamping levers. If said clamping means are released, the upper housing part 16 with the mixture supply tube 3 attached thereto can be lifted off from the lower housing part 17 and be lifted out of the centrifuge drum. To be able to remove the centrifuge drum 4, the hub piece 20 is locked by means of said latch 51, so that the impeller 11 attached thereto no longer can rotate. By rotating the centrifuge drum 4, the bayonet lock 19 thus is released and the centrifuge drum 4 can be removed.

Figure 8:
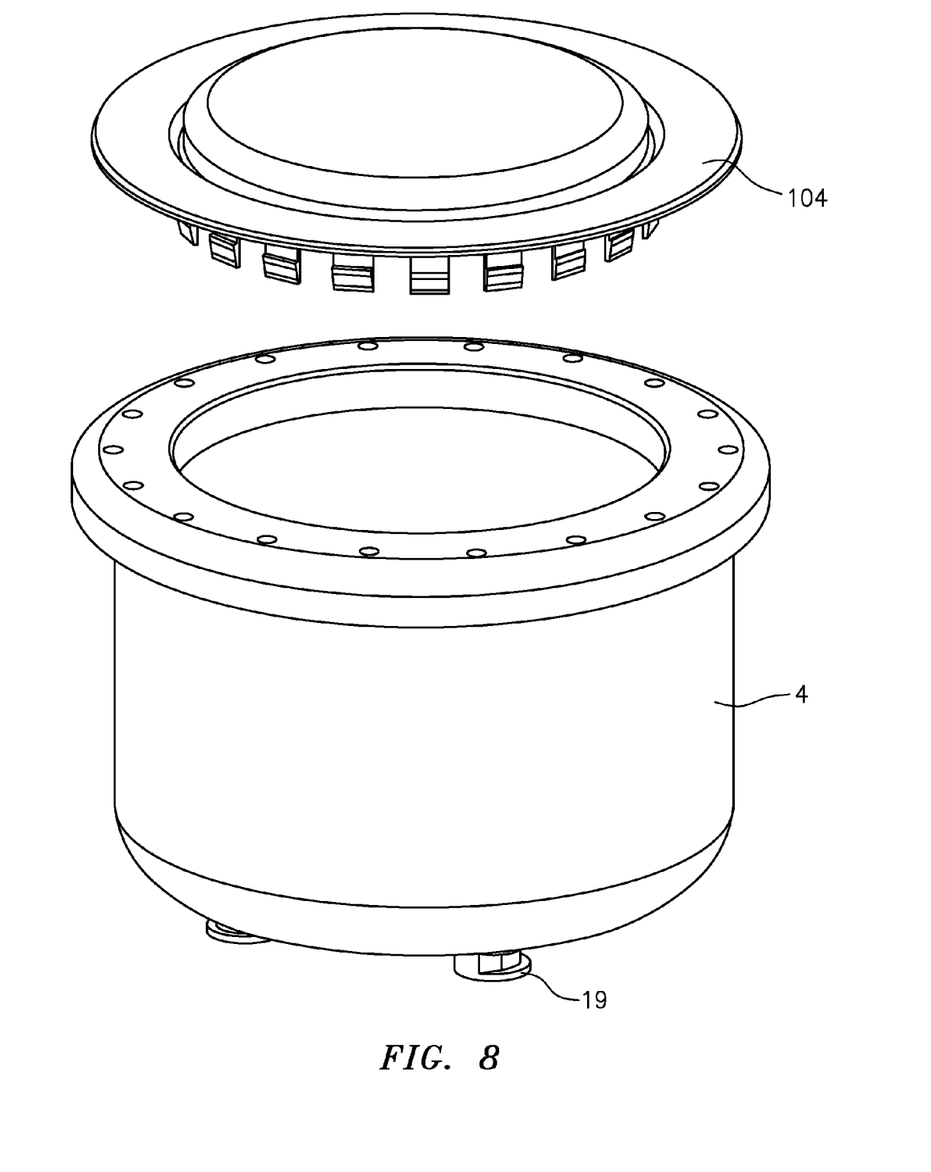
FIG. 8: shows a perspective view of the removed centrifuge drum of the separator in accordance with the embodiment of FIG. 4 in an exploded representation with an associated lid closing the centrifuge drum.
Figure 9:
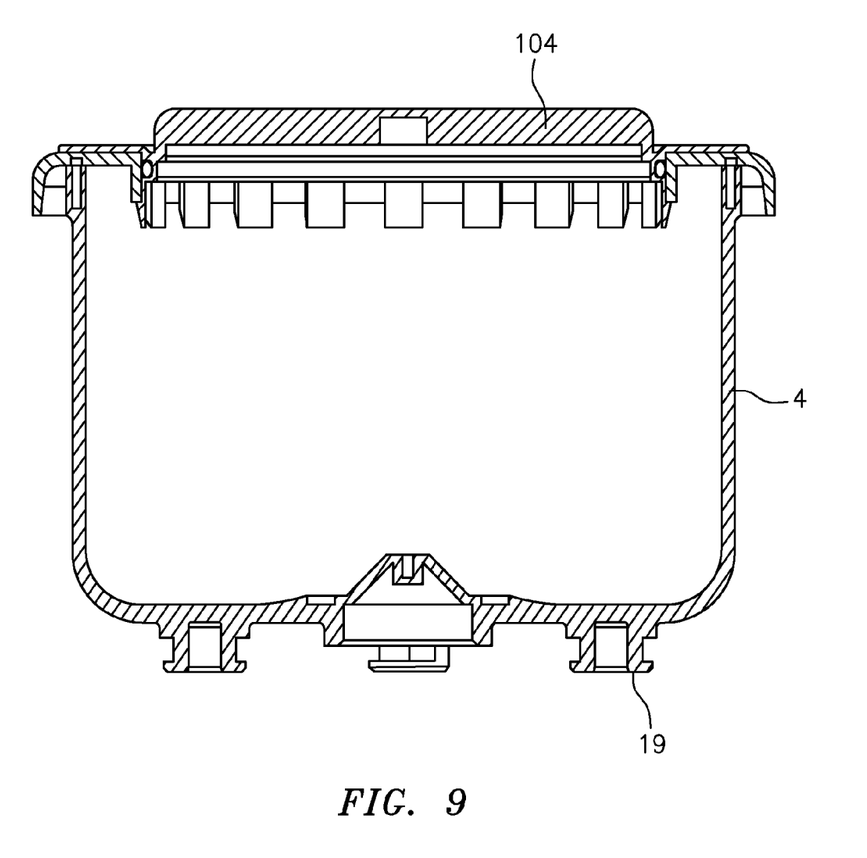
FIG. 9: shows a longitudinal section through the centrifuge drum from FIG. 8 with closed lid.

As shown in FIGS. 8 and 9, the centrifuge drum 4 has a contact surface which can be formed by the quick-acting locking means 19. Advantageously, the centrifuge drum 4 can be closed with a lid 104. Advantageously, the lid 104 can include latching means in the form of protruding latching tongues, by means of which it is positively held at the edge of the centrifuge drum, cf. FIG. 9. If a solids blocking flange is provided at the upper end of the centrifuge drum 4 in accordance with the embodiments of FIGS. 1 to 6, said lid 104 can be clamped or latched thereto.

Figure 7:
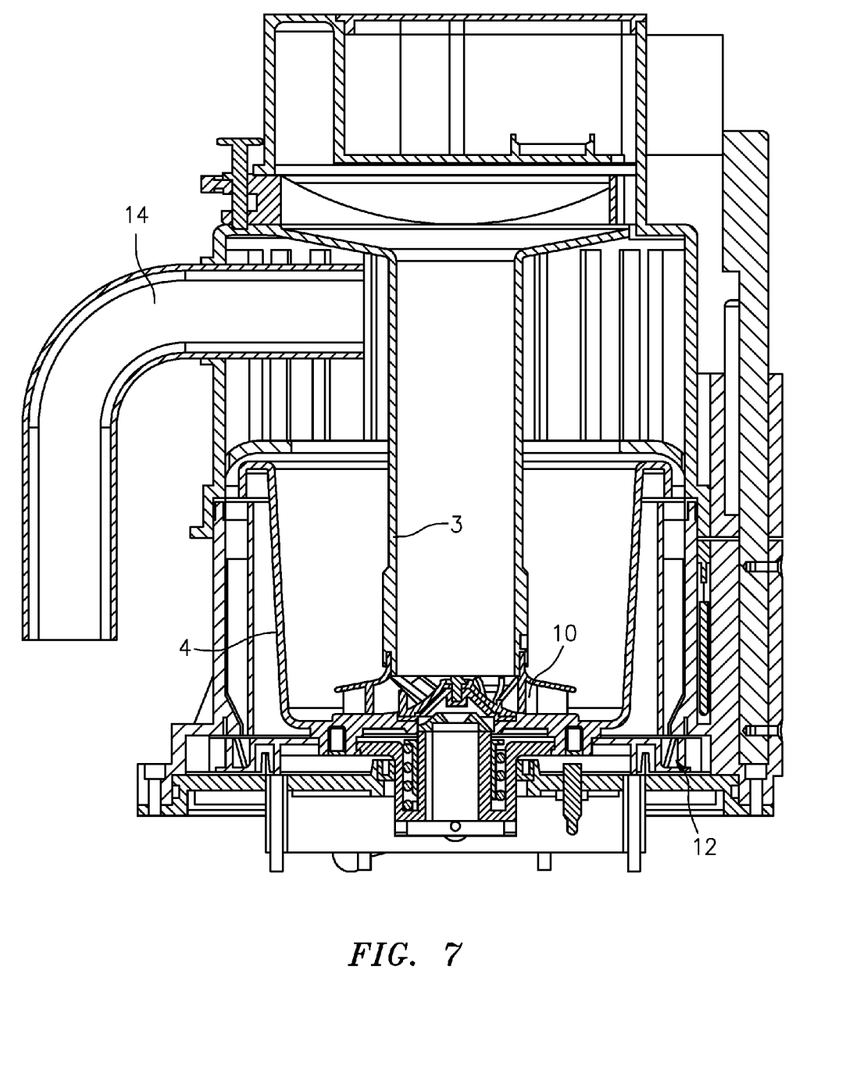
FIG. 7: shows a partial longitudinal section through a separator similar to FIG. 4 in accordance with another preferred embodiment of the invention, in which the centrifuge drum is formed without solids blocking flange.

FIG. 7 shows a further embodiment of a separator, essential parts of which correspond to the above-described embodiments, so that reference is made to their description. An essential difference over the embodiments of FIGS. 1 to 6 is the configuration of the centrifuge drum 4, which has no solids blocking flanges protruding to the inside on its inner shell surface. At the upper edge of the cup-shaped centrifuge drum 4, there is merely provided an overflow edge, over which the centrifuged water possibly containing solids can overflow, cf. FIG. 7.

The invention claimed is:

1. A separator for separating air and any present solids from a mixture of dental waste water, comprising
   an air-water separator (1) in turn comprising
   a centrifuge drum (4),
   a mixture supply tube (3) opening into the centrifuge drum (4),
   an air discharge duct (5) extending from the centrifuge drum (4) to the mixture supply tube (3),
   the centrifuge drum (4) having an upper draining edge (6*b*),
   a water outlet (8) guided over the upper draining edge (6*b*) onto and outside of the centrifuge drum (4),
   a central turbine wheel (10) positioned within the centrifuge drum (4) and into which the mixture supply tube (3) opens,
   the central turbine wheel (10) arranged adjacent a bottom (9) of the centrifuge drum (4), and
   a waste water delivery pump (12) having an impeller (11), communicating with the water outlet (8), and arranged adjacent both the outside of the centrifuge drum (4) and the centrifuge drum bottom (9).

2. The separator according to claim 1, wherein the air-water separator (1) is arranged in a solids separator (2), such that the air-water separator (1) and the solids separator (2) lie one inside the other, and the solids separator (2) includes at least one solids blocking flange (6) on a centrifuge drum shell surface (7).

3. The separator according to claim 1, wherein a waste water outlet (13) is arranged below the centrifuge drum bottom (9) approximately at the level of the impeller (11) and an air outlet (14) is arranged above the centrifuge drum (4).

4. The separator according to claim 1, wherein the centrifuge drum (4) is formed free from solids outlet openings.

5. The separator according to claim 1, wherein the turbine wheel (10), the centrifuge drum (4) and the impeller (11) of the waste water delivery pump (12) form a mounting unit (15) removable, as a whole, from a separator housing part (16) accommodating the mixture supply tube (3).

6. The separator according to claim 5, wherein the mounting unit includes a cup-shaped assembly carrier which forms a further separator housing part (17) and releasably attachable to the aforementioned separator housing part (16) and rotatably carries or accommodates the impeller (11) of the waste water delivery pump (13), the centrifuge drum (4) and the turbine wheel (10).

7. The separator according to claim 6, wherein the assembly carrier includes a central port for connection of a rotary drive (18).

8. The separator according to claim 1, wherein the centrifuge drum (4), the turbine wheel (10) and the impeller (11) are supported by a common central pivot bearing below the centrifuge drum bottom (9).

9. The separator according to claim 1, wherein the centrifuge drum (4) is attached with its bottom to the impeller (11) of the waste water delivery pump (12).

10. The separator according to claim 9, wherein a releasable quick-acting closure lock (19) to be actuated tool-free is provided for attachment of the centrifuge drum (4) to the impeller (11).

11. The separator according to claim 10, wherein the closure lock (19) is a spring-biased bayonet lock.

12. The separator according to claim 1, wherein the impeller (11) of the waste water delivery pump (12), the centrifuge drum (4) and the turbine wheel (10) are non-rotatably attached to a central hub or shaft piece (20) which includes a coupling piece (21) for coupling to a common rotary drive (18).

13. The separator according to claim 12, wherein the hub or shaft piece (20) is rotatably accommodated in an assembly carrier forming a further separator housing part (17), and the rotary drive (18) is releasably attachable to the assembly carrier by a housing portion and releasably couplable to a drive shaft (22) by the hub or shaft piece (20).

14. The separator according to claim 13, wherein the hub or shaft piece (20) is rigidly mounted on the drive shaft (22) and the assembly carrier is rigidly connectable with a rotary drive housing portion.

15. The separator according to claim 1, wherein the impeller (11) of the waste water delivery pump (12) includes a blade rim (23) arranged at the outer edge of the centrifuge drum bottom (9).

16. The separator according to claim 1, wherein the impeller (11) of the waste water delivery pump (12) includes an axial inlet region (24), onto which an annular portion of the water outlet (8) opens, which surrounds a centrifuge drum shell surface (7).

17. The separator according to claim 1, wherein the impeller (11) of the waste water delivery pump (12) has a radial outlet (25).

18. The separator according to claim 1, wherein the mixture supply tube (3) is accommodated in the air discharge duct (5).

19. The separator according to claim 18, wherein the mixture supply tube (3) is coaxially arranged with respect to the air discharge duct (5).

20. The separator according to claim 1, wherein the mixture supply tube (3) is arranged vertically and the turbine wheel (10) is rotatable with respect to the mixture supply tube (3).

21. The separator according to claim 1, wherein the turbine wheel (10) has an axial inlet region (26) and a radial outlet (27).

22. The separator according to claim 1, wherein the mixture supply tube (3) and the turbine wheel (10) annularly engage in each other.

23. The separator according to claim 1, wherein a plurality of solids blocking flanges (6a, 6b) arranged one above the other are provided in the centrifuge drum (4).

24. The separator according to claim 23, wherein the solids blocking flanges (6a, 6b) have different shapes.

25. The separator according to claim 1, wherein a solids blocking flange (6a) located closer to the centrifuge drum bottom (9) has an overflow edge located radially further to the inside than a solids blocking flange (6b) located further away from the centrifuge drum bottom (9).

26. The separator according to claim 25, wherein the solids blocking flange (6a) located closer to the centrifuge drum bottom (9) forms an inclined surface sloping radially inwards towards the centrifuge drum bottom (9), whereas the solids blocking flange (6b) located further away from the centrifuge drum bottom (9) has a bent cross-section with a hanging inner edge.

27. The separator according to claim 26, wherein the inclined surface is conical.

28. The separator according to claim 1, wherein the turbine wheel (10) is seated directly on the centrifuge drum bottom (9).

29. The separator according to claim 1, wherein the impeller (11) of the waste water delivery pump (12) is seated directly on the centrifuge drum bottom (9).

30. The separator according to claim 1, wherein the centrifuge drum bottom (9) is of the closed type.

31. The separator according to claim 1, wherein the mixture supply tube (3) is coaxial with an axis of the centrifuge drum (4) and annularly seated inside the central turbine wheel (10).

32. The separator according to claim 31, wherein the turbine wheel (10) is directly attached to the bottom (9) of the drum (4) which also forms part of a wall of the turbine wheel (10).

33. The separator according to claim 1, wherein the air discharge duct (5) is additionally arranged to at least partly constitute a cooling air duct for cooling a motor (18) driving the centrifuge drum (4).

34. A separator for separating air and any present solids from a mixture of dental waste water, comprising an air-water separator (1), wherein
a mixture supply tube (3) opens into a centrifuge drum (4),
an air discharge duct (5) extends from the centrifuge drum (4) to the mixture supply tube (3),
the centrifuge drum (4) has an upper draining edge over which a water outlet (8) is guided onto the outside of the centrifuge drum (4),
the air discharge duct (5) at least partly constitutes a cooling air duct for cooling a motor (18) driving the centrifuge drum (4), and
the air discharge duct (5) includes two half-shell-shaped cooling air duct portions (42, 43) traversed in opposite directions, which surround a winding (41) of the motor (18).

35. The separator according to claim 34, wherein the air discharge duct (5) is guided through a housing portion (40) accommodating the motor (18).

36. The separator according to claim 34, wherein the motor (18) is formed without a cooling fan wheel such that the centrifuge drum (4) and air discharge duct (5) constitute the sole mechanism for cooling the motor (18) via air sucked off from the centrifuge drum (4).

37. The separator according to claim 34, wherein the air discharge duct (5) is at least partly shielded with insulating elements (47) on its wall.

38. The separator according to claim 37, wherein the insulating elements (47) shield the air discharge duct (5) in the vicinity of its configuration as cooling air duct around the motor (18).

39. The separator according to claim 34, wherein a water remover (48) is provided for removing liquid separated in the centrifuge drum (4).

40. The separator according to claim 39, wherein the water remover (48) includes a temporary reservoir (49) for temporarily receiving the liquid removed from the centrifuge drum (4).

41. The separator according to claim 34, wherein the mixture supply tube (3) is coaxial with an axis of the centrifuge drum (4) and coaxially seated on an axle of the motor (18).

42. The separator according to claim 34, wherein
one of said half-shell shaped cooling duct portions (43) is connected with the air discharge duct (5), and additionally comprising a waste air duct (44) connected with the other of said half-shell shaped cooling duct portions (42), and a waste air blower (46) having a compressor wheel or impeller (45) connected with both said half-shell shaped cooling duct portions (42, 43) and arranged on a side of the motor (18) opposite the centrifuge drum (4), with the wheel or impeller (45) and the centrifuge drum (4) both seated on an axle of the motor (18).

43. A separator for separating air and any present solids from a mixture of dental waste water, comprising an air-water separator (1), wherein a mixture supply tube (3) opens into a centrifuge drum (4), an air discharge duct (5) extends from the centrifuge drum (4) to the mixture supply tube (3), the centrifuge drum (4) has an upper draining edge over which a water outlet (8) is guided onto the outside of the centrifuge drum (4), the air discharge duct (5) at least partly constitutes a cooling air duct for cooling a motor (18) driving the centrifuge drum (4), the air discharge duct (5) is guided through a housing portion (40) accommodating the motor (18), and the air discharge duct is guided through a winding (41) of the motor (18).

* * * * *